United States Patent [19]

Maurer et al.

[11] Patent Number: 4,666,894
[45] Date of Patent: May 19, 1987

[54] O-ETHYL O-ISOPROPYL O-(2-TERT.-BUTYLPRYRIMIDIN-5-YL)THIONOPHOSPHATE, COMPOSITION AND METHOD OF COMBATTING SOIL INSECTS WITH IT

[75] Inventors: Fritz Maurer, Wuppertal; Bernhard Homeyer, Leverkusen; Benedikt Becker, Mettmann, all of Fed. Rep. of Germany

[73] Assignee: Bayer Aktiengesellschaft, Leverkusen, Fed. Rep. of Germany

[21] Appl. No.: 606,106

[22] Filed: May 2, 1984

[30] Foreign Application Priority Data

May 17, 1983 [DE] Fed. Rep. of Germany ....... 3317824

[51] Int. Cl.$^4$ .................. A01N 57/16; C07F 9/65
[52] U.S. Cl. ........................................ 514/86; 544/243
[58] Field of Search ............... 544/243; 424/200; 514/86

[56] References Cited

U.S. PATENT DOCUMENTS

| 4,127,652 | 11/1978 | Maurer et al. | 424/200 |
| 4,325,948 | 4/1982 | Maurer et al. | 424/200 |
| 4,429,125 | 1/1984 | Reifschneider | 544/243 |
| 4,444,764 | 4/1984 | Reifschneider et al. | 424/200 |

FOREIGN PATENT DOCUMENTS

| 0004644 | 10/1979 | European Pat. Off. | 544/243 |
| 0009566 | 4/1980 | European Pat. Off. | |
| 3317824 | 11/1984 | Fed. Rep. of Germany | 544/243 |
| 2365577 | 4/1978 | France | |

*Primary Examiner*—Donald G. Daus
*Assistant Examiner*—Diana G. Rivers
*Attorney, Agent, or Firm*—Sprung Horn Kramer & Woods

[57] ABSTRACT

Pyrimidin-5-yl thionophosphate of the formula

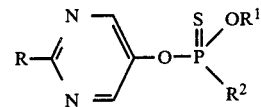

in which
R is alkyl or aryl,
R$^1$ is ethyl or i-propyl and
R$^2$ is i-propoxy-, sec.-butoxy or ethylamino, or
R$^1$ is n-propyl and at the same time R$^2$ is n-propoxy, which possess arthropodicidal activity.

3 Claims, No Drawings

O-ETHYL O-ISOPROPYL O-(2-TERT.-BUTYLPRYRIMIDIN-5-YL)THIONO-PHOSPHATE, COMPOSITION AND METHOD OF COMBATTING SOIL INSECTS WITH IT

The invention relates to new pyrimidin-5-yl thionophosphates, a process for their preparation and their use in pest-combating agents, in particular as arthropocides.

It is known that certain thionophosphoric acid esters or ester amides, such as, for example, O,O-diethyl O-(2-i-propyl-pyrimidin-5-yl), O-ethyl O-n-propyl O-(2-i-propyl-pyrimidin-5-yl) and O,O-diethyl O-(2-tert.-butyl-pyrimidin-5-yl)thionophosphate or O-ethyl-O-(2-i-propyl-pyrimidin-5-yl)-N-iso-propyl- and O-ethyl-O-(2-methyl-pyrimidin-5-yl)-N-ethyl-thionophosphoric acid ester-amide, have insecticidal activity. See U.S. Ser. No. 834,940 issued to U.S. Pat. No. 4,127,652 Nov. 28, 1978.

However, the action and the long-term action of these compounds are not always completely satisfactory, particularly in the case of certain insects and mites.

New pyrimidin-5-yl thionophosphates of the formula (I)

$$\text{R}-\underset{N=}{\overset{N}{\diagdown}}\!\!\!\!\diagup\!\!-\text{O}-\overset{\overset{S}{\|}}{\text{P}}\diagup\!\!\overset{OR^1}{\diagdown R^2} \quad (I)$$

in which
R represents alkyl or aryl,
$R^1$ represents ethyl or i-propyl and
$R^2$ represents i-propoxy-, sec.-butoxy or ethylamino, or
$R^1$ represents n-propyl and at the same time $R^2$ represents n-propoxy,
have now been found.

Furthermore, it has been found that the new substituted pyrimidin-5-yl thionophosphates of the formula (I) are obtained when 5-hydroxypyrimidines of the formula (II)

$$\text{R}-\underset{N=}{\overset{N}{\diagdown}}\!\!\!\!\diagup\!\!-\text{OH} \quad (II)$$

in which R has the meaning given above,
or the corresponding alkali metal, alkaline earth metal or ammonium salts, are reacted with halides of the formula (III)

$$\text{Hal}-\overset{\overset{S}{\|}}{\text{P}}\diagup\!\!\overset{OR^1}{\diagdown R^2} \quad (III)$$

ps in which
$R^1$ and $R^2$ have the meanings given above and
Hal represents halogen, such as chlorine or bromine, if appropriate in the presence of an acid acceptor and, if appropriate, in the presence of a diluent.

The new pyrimidin-5-yl thionophosphates of the formula (I) are distinguished in an outstanding manner by a particularly high and long activity as pest-combating agents, in particular as arthropocides.

The alkyl radical R can be branched or straight-chain, and contains 1 to 12, preferably 1 to 8, in particular 1 to 6, and particularly preferably 1 to 4, carbon atoms.

Methyl, ethyl, n-propyl, i-propyl, n-butyl, i-butyl, sec.-butyl and tert.-butyl may be mentioned as examples. Alkyl R preferably represents i-propyl and tert.-butyl.

Aryl R represents aryl having 6 to 10 carbon atoms, preferably phenyl or naphthyl, in particular phenyl.

The invention preferably relates to compounds of the formula (I) in which
R represents straight-chain or branched alkyl having 1 to 6 carbon atoms or aryl having 6 to 10 carbon atoms,
$R^1$ represents ethyl or i-propyl and
$R^2$ represents i-propoxy, sec.-butoxy or ethylamino, or
$R^1$ represents n-propyl and at the same time $R^2$ represents n-propoxy. Particularly preferred compounds of the formula (I) are those in which
R represents $C_1$-$C_4$-alkyl or phenyl,
$R^1$ represents ethyl or i-propyl and
$R^2$ represents i-propoxy, sec.-butoxy or ethylamino, or
$R^1$ represents n-propyl and at the same time $R^2$ represents n-propoxy. Very particularly preferred compounds of the formula (I) are those in which
R represents n-propyl, i-propyl, n-butyl, i-butyl, sec.-butyl, tert.-butyl and phenyl,
$R^1$ represents ethyl or i-propyl, and
$R^2$ represents i-propoxy, sec.-butoxy or ethylamino, or
$R^1$ represents n-propyl and at the same time $R^2$ represents n-propoxy. The compounds of the formula (I) in which
$R^1$ represents ethyl or -i.-propyl and
$R^2$ represents i-propoxy, sec.-butoxy or ethylamino, have particularly outstanding actions.

If, for example, O-ethyl-O-isopropyl-thionophosphoric acid diester-chloride and 5-hydroxy-2-phenyl-pyrimidine are used as starting materials for the process according to the invention, the corresponding reaction can be represented by the following equation:

$$\underset{N=}{\overset{N}{\diagdown}}\!\!\!\!\diagup\!\!-\text{OH} + \text{Cl}-\overset{\overset{S}{\|}}{\text{P}}\diagup\!\!\overset{OC_2H_5}{\diagdown O-iso-C_3H_7} \xrightarrow[-\text{HCl}]{+\text{ base}}$$

$$\underset{N=}{\overset{N}{\diagdown}}\!\!\!\!\diagup\!\!-\text{O}-\overset{\overset{S}{\|}}{\text{P}}\diagup\!\!\overset{OC_2H_5}{\diagdown O-iso-C_3H_7}$$

Formula (II) gives a definition of the 5-hydroxypyrimidines, or the corresponding alkali metal, alkaline earth metal or ammonium salts, to be employed in the process according to the invention as starting materials for the preparation of the new compounds of the formula (I). In this formula, R represents those radicals which are given above in the definition in formula (I). The sodium, potassium or calcium salts are preferably employed as alkali metal or alkaline earth metal salts.

The compounds of the formula (II) are known, and or can be prepared by generally known processes and methods (see for example DE-OS (German Published Specification) No. 2,643,262, DE-OS (German Published Specification) No. 2,706,127 and J. Chem. Soc. 1960, 4590).

The following may be mentioned as examples of the compounds of the formula (II): 2-methyl-, 2-ethyl-, 2-n-propyl-, 2-i-propyl-, 2-n-butyl-, 2-i-butyl-, 2-sec.-butyl-, 2-tert.-butyl- and 2-phenyl-5-hydroxypyrimidine and the corresponding sodium, potassium, calcium and ammonium salts.

Formula (III) gives a definition of the halides furthermore to be employed as starting materials. In this formula, $R^1$ and $R^2$ represent those radicals which are given in the definition in formula (I). In this formula, Hal represents halogen, such as, in particular, chlorine or bromine.

The compounds of the formula (III) are known.

The following may be mentioned as examples of the halides of the formula (III):

O-ethyl-O-iso-propyl-, O-ethyl-O-sec.-butyl-, O-di-iso-propyl- and O-sec.-butyl-O-iso-propyl-thionophosphoric acid ester chloride or bromide;

O-ethyl-N-ethyl- and O-i-propyl-N-ethyl-thionophosphoric acid ester-amide chloride or bromide.

The process, according to the invention, for the preparation of the new pyridimidin-5-yl thionophosphates of the formula (I) is preferably carried out using diluents. Suitable diluents are virtually all inert organic solvents.

These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric acid triamide.

The process can, if appropriate, be carried out in the presence of acid acceptors. All customary acid-binding agents can be used as acid acceptors. Alkali metal carbonates and alcoholates, such as sodium carbonate and potassium carbonate, sodium methylate, potassium methylate, sodium ethylate and potassium ethylate, alkali metal hydrides, such as sodium hydride, and aliphatic, aromatic or heterocyclic amines, for example triethylamine, trimethylamine, dimethylaniline, dimethylbenzylamine and pyridine, have proved particularly useful.

The process according to the invention is carried out in general at temperatures between 0° C. and 100° C. The range between 20° C. and 80° C. is preferred. The reactions are carried out in general under atmospheric pressure.

To carry out the process according to the invention, the starting materials are usually employed in approximately equimolar amounts. An excess of one or the other of the reactants does not have any substantial advantages. The reaction is carried out in general in a suitable diluent, in the presence of an acid acceptor, and the reaction mixture is stirred for several hours at the required temperature. Thereafter, an organic solvent, for example toluene, is added, and the organic phase is worked up in a customary manner by washing, drying and distilling off the solvent.

The new compounds are obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. They are characterized by their refractive index.

The active compounds are well tolerated by plants, have a favorable level of toxicity to warm-blooded animals, and are suitable for combating animals pests, especially insects and arachnida, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, Pectinophora gossypiella, *Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Certatitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation examples which follow are intended to illustrate the process according to the invention:

EXAMPLE 1

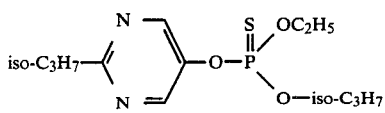

A mixture of 300 ml of acetonitrile, 13.8 g (0.1 mol) of 5-hydroxy-2-iso-propyl-pyrimidine, 20.7 g (0.15 mol) of potassium carbonate and 20.2 g (0.1 mol) of O-ethyl-O-iso-propyl-thionophosphoric acid diester chloride is stirred for 2 hours at 45° C. Thereafter, the reaction mixture is poured into 400 ml of toluene, and the solution is washed with twice 300 ml of water. The toluene solution is dried over sodium sulphate and evaporated down in vacuo. The residue is distilled in a high vacuum.

In this manner, 28 g (92% of theory) of O-ethyl O-iso-propyl O-(2-iso-propyl-pyrimidin-5-yl)thionophosphate are obtained in the form of a yellow oil having a refractive index $n_D^{23}$: 1.4910.

The following compounds of the formula

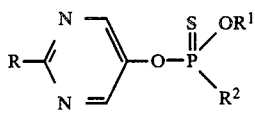

can be prepared in an analogous manner:

| Example No. | R | $R^1$ | $R^2$ | Refractive index |
|---|---|---|---|---|
| 2 | —iso-$C_3H_7$ | —iso-$C_3H_7$ | —O—iso-$C_3H_7$ | $n_D^{20}$: 1.4869 |
| 3 | —tert.-$C_4H_9$ | —$C_2H_5$ | —O—iso-$C_3H_7$ | $n_D^{20}$: 1.4917 |
| 4 | —iso-$C_3H_7$ | —$C_2H_5$ | —O—sec.-$C_4H_9$ | $n_D^{20}$: 1.4960 |
| 5 | —tert.-$C_4H_9$ | —$C_2H_5$ | —O—sec.-$C_4H_9$ | $n_D^{22}$: 1.4935 |
| 6 | —tert.-$C_4H_9$ | —iso-$C_3H_7$ | —O—iso-$C_3H_7$ | $n_D^{22}$: 1.4857 |
| 7 | —C$_6$H$_5$ | —$C_2H_5$ | —O—iso-$C_3H_7$ | $n_D^{22}$: 1.5516 |
| 8 | —tert.-$C_4H_9$ | —$C_2H_5$ | —NH$C_2H_5$ | $n_D^{21}$: 1.5100 |
| 9 | —C$_6$H$_5$ | —$C_2H_5$ | —O—sec.-$C_4H_9$ | |
| 10 | —C$_6$H$_5$ | —iso-$C_3H_7$ | —O—iso-$C_3H_7$ | |
| 11 | —iso-$C_3H_7$ | —n-$C_3H_7$ | —O—n-$C_3H_7$ | $n_D^{23}$: 1.4915 |

The examples which follow are intended to illustrate the biological activity of the compounds according to the invention:

EXAMPLE A

Long-term action test/soil insects

Test insect: *Phorbia antiqua* grubs
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of the active compound is intimately mixed with soil. The concentration of the active compound in the preparation is of practically no importance, only the amount by weight of active compound per unit volume of soil, which is given in ppm (mg/1), being decisive. The soil is filled into 5 1 pots and the pots are left to stand at 20° C.

After an interval of 2 weeks, soil samples of 250 ccm are taken, after once again mixing thoroughly, and the appropriate test insects are placed in the treated soil. After a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of preparation examples (1), (3), (8) and (11), for example at an active compound concentration of 2.5 ppm, show a destruction of 100% after 5 weeks.

EXAMPLE B

Drosophila test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

1 cm$^3$ of the preparation of the active compound is pipetted onto a filter paper disc (7 cm diameter). The wet disc is placed over the opening of a glass vessel containing 50 vinegar flies (*Drosophila melanogaster*) and is covered with a glass plate.

After the specified period of time, the destruction in % is determined. 100% means that all the flies have been killed; 0% means that none of the flies have been killed.

In this test, the compounds from preparation examples (1), (2), (3), (4), (5), (6), (8) and (11), for example at an active compound concentration of 0.01%, show a destruction of 100% after one day.

EXAMPLE C

Plutella test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) as long as the leaves are still moist.

After the specified period of time, the destruction in % is determined. 100% means that all the caterpillars have been killed; 0% means that none of the caterpillars have been killed.

In this test, the compounds from preparation examples (1), (2), (3), (4), (5), (6), (7), (8) and (11), for example at an active compound concentration of 0.1%, show a destruction of 100% after 3 days.

EXAMPLE D

Tetranychus test (resistant)

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified period of time, the destruction in % is determined. 100% means that all the spider mites have been killed; 0% means that none of the spider mites have been killed.

In this test, the compounds from preparation examples (1) and (8), for example at an active compound concentration of 0.1%, show a destruction of 100% after 2 days.

It is understood that the specification and examples are illustrative but not limitative of the present invention and that other embodiments within the spirit and scope of the invention will suggest themselves to those skilled in the art.

We claim:

1. The compound O-ethyl O-isopropyl O-(2-tert.-butyl-pyrimidin-5-yl)thionophosphate of the formula

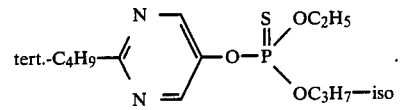

2. An arthropodicidal composition comprising an arthropodicidally effective amount of the compound according to claim 1 in admixture with a diluent.

3. A method of combatting soil insects which comprises applying to such soil insects or to a field in which there is being grown a crop susceptible to soil insects a soil insecticidally effective amount of the compound according to claim 1.

* * * * *